(12) United States Patent
Amino et al.

(10) Patent No.: US 6,548,096 B1
(45) Date of Patent: Apr. 15, 2003

(54) ASPARTYL DIPEPTIDE ESTER DERIVATIVES AND SWEETENERS

(75) Inventors: Yusuke Amino, Kawasaki (JP);
Kazuko Yuzawa, Kawasaki (JP);
Tadashi Takemoto, Kawasaki (JP);
Ryoichiro Nakamura, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/684,940

(22) Filed: Oct. 10, 2000

Related U.S. Application Data

(63) Continuation of application No. PCT/JP99/01210, filed on Mar. 11, 1999.

(30) Foreign Application Priority Data

| Apr. 9, 1998 | (JP) | 10-097701 |
| Feb. 17, 1999 | (JP) | 11-038190 |

(51) Int. Cl.[7] ............... A23L 1/236; C07C 229/00
(52) U.S. Cl. ............... 426/548; 560/41; 562/433
(58) Field of Search ............... 426/548, 2, 3, 426/660; 562/409, 433, 442, 450; 560/41

(56) References Cited

U.S. PATENT DOCUMENTS 5,480,668 A * 1/1996 Nofre et al. ............ 426/548
5,968,581 A   10/1999 Nakamura et al.

FOREIGN PATENT DOCUMENTS

| JP | 260673 | 10/1995 |
| JP | 8-503206 | 4/1996 |
| WO | WO99/52937 | 10/1999 |

* cited by examiner

Primary Examiner—Leslie Wong
(74) Attorney, Agent, or Firm—Oblon, Spivak, McClelland, Maier & Neustadt, P.C.

(57) ABSTRACT

Low-calory sweeteners comprising novel aspartyl dipeptide ester derivatives and their salts have a sweetening potency of up to 35000 times that of sugar and include compounds such as N-[N-[3-(3-methyl-4-hydroxyphenyl)propyl]-L-α-aspartyl]-L-phenylalanine 1-methyl ester and N-[N-[3-(3-hydroxy-4-methoxyphenyl)propyl]-L-α-aspartyl]-L-phenylalanine 1-methyl ester.

53 Claims, No Drawings

ASPARTYL DIPEPTIDE ESTER DERIVATIVES AND SWEETENERS

This application is a continuation of PCT/JP99/01210, filed Mar. 11, 1999.

BACKGROUND OF THE INVENTION

1. Field of the Invention

The present invention relates to novel aspartyl dipeptide ester derivatives, a sweetener and products such as foods which contain the sweetener.

2. Discussion of the Background

Fatness caused by excessive intake of sugar and diseases accompanied by fatness have been at issue in recent years, as eating habits have improved. Accordingly, a low-calorie sweetener that replaces sugar has been in demand. Aspartame is a widely used sweetener which has excellent safety and taste properties. However, aspartame is not very stable.

WO 94/1139 discloses that derivatives having an alkyl substituted amino group in aspartic acid exhibit improved sweetening potency and slightly improved stability. The best compound described in this document is N-[N-(3,3-dimethylbutyl)-L-α-aspartyl ]-L-phenylalanine 1-methyl ester having a 3,3-dimethylbutyl group as an alkyl group. The sweetening potency of this compound is 10,000 times that of sugar.

Other aspartame derivatives having 20 other types of substituents are described in above reference. However, their sweetening potency is reported to be less than 2,500 times that of sugar. Derivatives having a 3-(substituted phenyl)propyl group as an alkyl group are also disclosed. However, the sweetening potency of N-[N-(3-phenylpropyl)-L-α-aspartyl ]-L-phenylalanine 1-methyl ester is 1,500 times and that of N-[N-[3-(3-methoxy-4-hydroxyphenyl)propyl]-L-α-aspartyl]-L-phenylalanine 1-methyl ester is 2,500 times that of sugar. Thus, their sweetening potency is far less than that of N-[N-(3,3-dimethylbutyl)-L-α-aspartyl]-L-phenylalanine 1-methyl ester (10,000 times). (U.S. Pat. No. 5,480,668 is the equivalent to WO 94/1139).

SUMMARY OF THE INVENTION

It is an object of the invention to provide novel aspartyl dipeptide ester derivatives which are safe and have a sweetening potency equal to or higher than that of the N-[N-(3, 3-dimethylbutyl)-L-α-aspartyl]-L-phenylalanine 1-methyl ester.

It is another object of the present invention to provide a low-calorie sweetener containing the novel derivatives as an active ingredient.

These and other objects are achieved according to the invention, the first embodiment of which includes a compound of Formula (1):

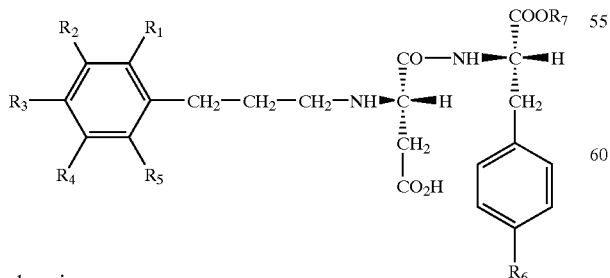

(1)

wherein
R₁, R₂, R₃, R₄ and R₅, independently represent a substituent selected from the group consisting of a hydrogen atom, a hydroxyl group, an alkoxy group having from 1 to 3 carbon atoms, an alkyl group having from 1 to 3 carbon atoms and a hydroxyalkyloxy group having 2 or 3 carbon atoms; or R₁ and R₂, or R₂ and R₃ together form a methylenedioxy group, wherein R₄, R₅, and R₁ or R₃ which do not form said methylenedioxy group independently represent a substituent selected from the group consisting of a hydrogen atom, a hydroxyl group, an alkoxy group having from 1 to 3 carbon atoms, an alkyl group having from 1 to 3 carbon atoms and a hydroxyalkyloxy group having 2 or 3 carbon atoms;

R₆ represents a hydrogen atom or a hydroxyl group; and

R₇ represents a substituent selected from the group consisting of a methyl group, an ethyl group, an isopropyl group, an n-propyl group and a t-butyl group;

wherein R₁ to R₅ do not all represent hydrogen atoms; and wherein R₂ or R₄ do not represent a methoxy group if R₃ represents a hydroxyl group; and the salt thereof.

DETAILED DESCRIPTION OF THE PREFERRED EMBODIMENTS

In order to achieve above objects, the present inventors have synthesized several aspartame derivatives in which various 3-(substituted phenyl) propyl groups are introduced into an amino group of aspartic acid using cinnamaldehyde having various substituents and 3-phenylpropianaldehyde having various substituents.

The inventors have examined the sweetening potency of above aspartame derivatives. They have found that their sweetening potency is far higher than that of N-[N-(3-phenylpropyl)-L-α-aspartyl]-L-phenylalanine-1-methyl ester and N-[N-(3,3-dimethylbutyl)-L-α-aspartyl]-L-phenylalanine 1-methyl ester. For example, N-[N-(3,3-dimethylbutyl)-L-α-aspartyl]-L-phenylalanine 1-methyl ester has a sweetening potency of 10,000 times that of sugar and N-[N-(3-phenylpropyl)-L-α-aspartyl]-L-phenylalanine-1-methyl ester has a sweetening potency of 1,500 times that of sugar (WO94/11391). The compounds represented by Formula (1), below, are excellent as a sweetener. These findings have led to the completion of the invention.

The novel aspartyl dipeptide ester derivatives of the invention include the compounds represented by Formula (1) and salts thereof.

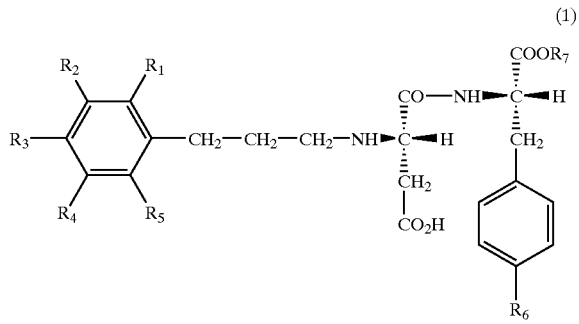

(1)

wherein
R₁, R₂, R₃, R₄ and R₅, independently from each other, represent a substituent selected from a hydrogen atom (H), a hydroxyl group (OH), an alkoxy group (OR; methoxy group, ethoxy group, propoxy groups, or the like) having from 1 to 3 carbon atoms, an alkyl group (R; methyl group, ethyl group, propyl groups, or the like) having from 1 to 3 carbon atoms and a hydroxyalkyloxy group (for example, $O(CH_2)_2OH$ or $OCH_2CH(OH)CH_3$) having 2 or 3 carbon atoms, or $R_1$ and $R_2$, or $R_2$ and $R_3$ together form a methylenedioxy group ($OCH_2O$);

wherein $R_4$, $R_5$ and, $R_1$ or $R_3$ which does not form the methylenedioxy group as a part thereof, independently from each other, represent any substituents as mentioned above designated for the $R_1$, $R_3$, $R_4$ and $R_5$, respectively, provided the case where $R_1$ to $R_5$ are all hydrogen atoms and the case where $R_2$ is a methoxy group and $R_3$ is a hydroxyl group and the case where $R_4$ is a methoxy group and $R_3$ is a hydroxyl group are excluded, $R_6$ represents a hydrogen atom or a hydroxyl group, and $R_7$ represents a substituent selected from a methyl group ($CH_3$), an ethyl group ($CH_2CH_3$), an isopropyl group ($CH(CH_3)_2$), an n-propyl group ($CH_2CH_2CH_3$) and a t-butyl group ($C(CH_3)_3$).

Amino acids constituting the derivatives are preferably L-isomers since L-isomers are present in nature.

With respect to the compounds of the invention, the following inventions are preferably included.

[1] Compounds of Formula (1)

wherein $R_3$ is a substituent selected from a hydroxyl group, an alkoxy group having from 1 to 3 carbon atoms, an alkyl group having from 1 to 3 carbon atoms and a hydroxyalkyloxy group having 2 or 3 carbon atoms, $R_1$, $R_2$, $R_4$ and $R_5$ are, independently from each other, each a substituent selected from a hydrogen atom, a hydroxyl group, an alkoxy group having from 1 to 3 carbon atoms, an alkyl group having from 1 to 3 carbon atoms and a hydroxyalkyloxy group having 2 or 3 carbon atoms, or $R_1$ and $R_2$, or $R_2$ and $R_3$ together form a methylenedioxy group ($OCH_2O$)

wherein $R_4$, $R_5$ and, $R_1$ or $R_3$ which does not form the methylenedioxy group as a part thereof, independently from each other, represent any substituents as mentioned above for the $R_1$, $R_3$, $R_4$ and $R_5$;

$R_6$ is a hydrogen atom or a hydroxyl group, and $R_7$ is a substituent selected from a methyl group, an ethyl group, an isopropyl group, an n-propyl group and a t-butyl group.

[2] Compounds of Formula (1)

wherein $R_3$ is a hydrogen atom, $R_1$, $R_2$, $R_4$ and $R_5$ are, independently from each other, each a substituent selected from a hydroxyl group, an alkoxy group having from 1 to 3 carbon atoms, an alkyl group having from 1 to 3 carbon atoms and a hydroxyalkyloxy group having 2 or 3 carbon atoms, or $R_1$ and $R_2$, or $R_2$ and $R_3$ together form a methylenedioxy group ($OCH_2O$)

wherein $R_4$, $R_5$ and, $R_1$ or $R_3$ which does not form the methylenedioxy group as a part thereof, independently from each other, represent any substituents as mentioned above designated for the $R_1$, $R_3$, $R_4$ and $R_5$, respectively, $R_6$ is a hydrogen atom or a hydroxyl group, and $R_7$ is a substituent selected from a methyl group, an ethyl group, an isopropyl group, an n-propyl group and a t-butyl group.

[3] Compounds of Formula (1)

wherein $R_3$ is a hydroxyl group, $R_1$, $R_2$, $R_4$ and $R_5$ are each a substituent selected from a hydrogen atom, a hydroxyl group, an alkoxy group having from 1 to 3 carbon atoms, an alkyl group having from 1 to 3 carbon atoms and a hydroxyalkyloxy group having 2 or 3 carbon atoms, or $R_1$ and $R_2$, or $R_2$ and $R_3$ together form a methylenedioxy group ($OCH_2O$)

wherein $R_4$, $R_5$, and $R_1$ or $R_3$ which does not form the methylenedioxy group as a part thereof, independently from each other, represent any substituents as mentioned above designated for the $R_1$, $R_3$, $R_4$ and $R_5$, respectively, $R_6$ is a hydrogen atom or a hydroxyl group, and $R_7$ is a substituent selected from a methyl group, an ethyl group, an isopropyl group, an n-propyl group and a t-butyl group.

[4] Compounds of Formula (1)

wherein $R_2$ is a hydroxyl group, $R_3$ is a methoxy group, $R_1$, $R_4$, $R_5$ and $R_6$ are each a hydrogen atom, and $R_7$ is a methyl group.

[5] Compounds of Formula (1) wherein $R_2$ and $R_3$ are each a methoxy group, $R_1$, $R_4$, $R_5$ and $R_6$ are each a hydrogen atom, and $R_7$ is a methyl group.

[6] Compounds of Formula (1)

wherein $R_2$ and $R_3$ together form a methylenedioxy group, $R_1$, $R_4$, $R_5$ and $R_6$ are each a hydrogen atom, and $R_7$ is a methyl group.

[7] Compounds of Formula (1)

wherein $R_3$ is a hydroxyl group, $R_1$, $R_2$, $R_4$, $R_5$ and $R_6$ are each a hydrogen atom, and $R_7$ is a methyl group.

[8] Compounds of Formula (1)

wherein $R_3$ is a methoxy group, $R_1$, $R_2$, $R_4$, $R_5$ and $R_6$ are each a hydrogen atom, and $R_7$ is a methyl group.

[9] Compounds of Formula (1)

wherein $R_3$ is an ethoxy group, $R_1$, $R_2$, $R_4$, $R_5$ and $R_6$ are each a hydrogen atom, and $R_7$ is a methyl group.

[10] Compounds of Formula (1)

wherein $R_2$ is a hydroxyl group, $R_1$, $R_2$, $R_4$, $R_5$ and $R_6$ are each a hydrogen atom, and $R_7$ is a methyl group.

[11] Compounds of Formula (1)

wherein $R_2$ is a methoxy group, $R_1$, $R_2$, $R_4$, $R_5$ and $R_6$ are each a hydrogen atom, and $R_7$ is a methyl group.

[12] Compounds of Formula (1)

wherein $R_3$ is a methoxy group, $R_2$ and $R_6$ are each a hydroxyl group, $R_1$, $R_4$ and $R_5$ are each a hydrogen atom, and $R_7$ is a methyl group.

[13] Compounds of Formula (1)
wherein $R_1$ is a hydroxyl group,
$R_3$ is a methoxy group,
$R_2$, $R_4$, $R_5$ and $R_6$ are each a hydrogen atom, and
$R_7$ is a methyl group.
[14] Compounds of Formula (1)
wherein $R_1$ is a hydroxyl group,
$R_2$ is a methoxy group,
$R_3$, $R_4$, $R_5$ and $R_6$ are each a hydrogen atom, and
$R_7$ is a methyl group.
[15] Compounds of Formula (1)
wherein $R_1$ is a hydroxyl group,
$R_4$ is a methoxy group,
$R_2$, $R_3$, $R_5$ and $R_6$ are each a hydrogen atom, and
$R_7$ is a methyl group.
[16] Compounds of Formula (1)
wherein $R_1$ is a hydroxyl group,
$R_3$ and $R_7$ are each a methyl group, and
$R_2$, $R_4$, $R_5$ and $R_6$ are each a hydrogen atom.
[17] Compounds of Formula (1)
wherein $R_1$ and $R_3$ are each a methoxy group,
$R_2$, $R_4$, $R_5$ and $R_6$ are each a hydrogen atom, and
$R_7$ is a methyl group.
[18] Compounds of Formula (1)
wherein $R_1$ is an ethoxy group,
$R_3$ is a methoxy group,
$R_2$, $R_4$, $R_5$ and $R_6$ are each a hydrogen atom, and
$R_7$ is a methyl group.
[19] Compounds of Formula (1)
wherein $R_2$ and $R_7$ are each a methyl group,
$R_3$ is a hydroxyl group, and
$R_1$, $R_4$, $R_5$ and $R_6$ are each a hydrogen atom.
[20] Compounds of Formula (1)
wherein $R_2$ is a hydroxyl group,
$R_3$ and $R_7$ are each a methyl group, and
$R_1$, $R_4$, $R_5$ and $R_6$ are each a hydrogen atom.
[21] Compounds of Formula (1)
wherein $R_2$ and $R_7$ are each a methyl group,
$R_3$ is a methoxy group, and
$R_1$, $R_4$, $R_5$ and $R_6$ are each a hydrogen atom.
[22] Compounds of Formula (1)
wherein $R_2$ and $R_4$ are each a methoxy group,
$R_1$, $R_3$, $R_5$ and $R_6$ are each a hydrogen atom, and
$R_7$ is a methyl group.
[23] Compounds of Formula (1)
wherein $R_3$ is a 2-hydroxyethoxy group,
$R_1$, $R_2$, $R_4$, $R_5$ and $R_6$ are each a hydrogen atom, and
$R_7$ is a methyl group.
[24] Compounds of Formula (1)
wherein $R_3$ and $R_7$ are each a methyl group, and
$R_1$, $R_2$, $R_4$, $R_5$ and $R_6$ are each a hydrogen atom.
Preferred salts of the compounds of Formula (1) are, for example, salts with alkali metals such as sodium and potassium; salts with alkaline earth metals such as calcium and magnesium; ammonium salts; salts with amino acids such as lysine and arginine; salts with inorganic acids such as hydrochloric acid and sulfuric acid; and salts with organic acids such as citric acid and acetic acid; and salts with saccharin, acesulfame, cyclamic acid and glycyrrhizic (glycyrrhizinic) acid. These salts are included in the present invention.

The aspartyl dipeptide ester derivatives of the invention can easily be formed by reductively alkylating aspartame derivatives with cinnamaldehydes having various substituents and a reducing agent. Preferably, the reducing agent is a hydrogen/palladium carbon catalyst. Aspartame derivatives can be obtained by the usual peptide synthesis method (Izumiya et al., Basis of Peptide Synthesis and Experiments Thereof, Maruzen, published Jan. 20, 1985). Alternatively, the derivatives can be formed by subjecting aspartame derivatives (for example, β-O-benzyl-α-L-aspartyl-L-phenylalanine methyl ester) having a protective group in a carboxylic acid in the β-position to reductive alkylation with cinnamaldehydes having various substituents and a reducing agent (for example, NaB(OAc)$_3$H) (A. F. Abdel-Magid et al., Tetrahedron Letters, 31, 5595 (1990)), and then removing the protective group. However, the method of forming the compounds of the invention is not limited thereto. 3-Phenylpropionaldehydes having various substituents or acetal derivatives thereof can be used as precursor aldehydes in the reductive alkylation instead of cinnamaldehydes having various substituents.

As a result of a sensory evaluation, the compounds and the salts thereof in the invention were found to have a strong sweetening potency and have taste properties similar to that of sugar. For example, the sweetening potency of N-[N-[3 (3-methyl-4-hydroxyphenyl)propyl]-L-α-aspartyl]-L-phenylalanine 1-methyl ester was approximately 35,000 times that of sugar; that of N-[N-[3-(2-hydroxy-4-methylphenyl)propyl]-L-α-aspartyl]-L-α-phenylalanine 1-methyl ester was approximately 30,000 times that of sugar; that of N-[N-[3-(3-hydroxy-4-methoxyphenyl) propyl]-L-α-aspartyl]-L-phenylalanine 1-methyl ester was approximately 20,000 times that of sugar; that of N-[N-[3-(2-hydroxy-4-methoxyphenyl)propyl]-L-α-aspartyl]-L-phenylalanine 1-methyl ester was approximately 20,000 times that of sugar; that of N-[N-[3-(3-hydroxy-4-methylphenyl)propyl]-L-α-aspartyl]-L-phenylalanine 1-methyl ester was approximately 15,000 times that of sugar; that of N-(N-(3-(3-hydroxyphenyl)propyl]-L-α-aspartyl]-L-phenylalanine 1-methyl ester was approximately 8,000 times that of sugar; that of N-[N-(3-(4-methoxyphenyl)propyl]-L-α-aspartyl]-L-phenylalanine 1-methyl ester was approximately 6,500 times that of sugar; and that of N-(N-[3-(3-hydroxy-4-methoxyphenyl)propyl]-L-α-aspartyl]-L-tyrosine 1-methyl ester was approximately 16,000 times that of sugar.

The structures and the results of the sensory evaluation of aspartyl dipeptide derivatives represented by formula (2) are shown in Table 1.

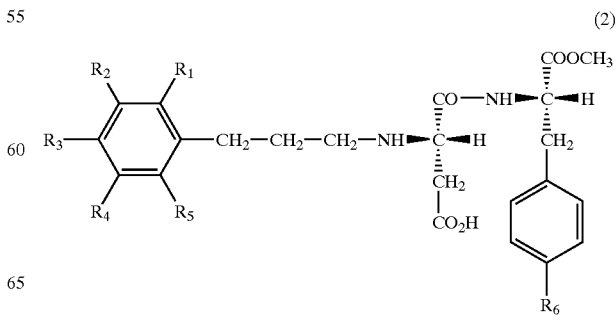

(2)

TABLE 1

Structures and sweetening potency of aspartyl dipeptide ester derivatives

| Compound No. | $R_1$ | $R_2$ | $R_3$ | $R_4$ | $R_5$ | $R_6$ | sweetening potency*) |
|---|---|---|---|---|---|---|---|
| 1 | H | OH | $OCH_3$ | H | H | H | 20000 |
| 2 | H | $OCH_3$ | $OCH_3$ | H | H | H | 2500 |
| 3 | H | $OCH_2O$ | | H | H | H | 5000 |
| 4 | H | H | OH | H | H | H | 5000 |
| 5 | H | H | $OCH_3$ | H | H | H | 6500 |
| 6 | H | H | $OCH_2CH_3$ | H | H | H | 1500 |
| 7 | H | OH | H | H | H | H | 8000 |
| 8 | H | $OCH_3$ | H | H | H | H | 3500 |
| 9 | H | OH | $OCH_3$ | H | H | OH | 16000 |
| 10 | OH | H | $OCH_3$ | H | H | H | 20000 |
| 11 | OH | $OCH_3$ | H | H | H | H | 10000 |
| 12 | OH | H | H | $OCH_3$ | H | H | 1500 |
| 13 | OH | H | $CH_3$ | H | H | H | 30000 |
| 14 | $OCH_3$ | H | $OCH_3$ | H | H | H | 4000 |
| 15 | $OCH_2CH_3$ | H | $OCH_3$ | H | H | H | 2500 |
| 16 | H | $CH_3$ | OH | H | H | H | 35000 |
| 17 | H | OH | $CH_3$ | H | H | H | 15000 |
| 18 | H | $CH_3$ | $OCH_3$ | H | H | H | 8000 |
| 19 | H | $OCH_3$ | H | $OCH_3$ | H | H | 800 |
| 20 | H | H | $OCH_2CH_2OH$ | H | H | H | 1000 |
| 21 | H | H | $CH_3$ | H | H | H | 4000 |

*)Relative to sweetening potency of a 4% sucrose aqueous solution

As demonstrated by the results of Table 1, the novel derivatives in the present invention are excellent in sweetening potency.

The compounds of the invention and their salts are used as a sweetener, singly or in combination with other sweeteners unless particular problems arise. The sweetening potency of the sweetener is preferably in the range of from 800 to 35,000 times that of sugar, and more preferably of from 15,000 to 35,000 times that of sugar. The sweetening potency includes all values and subvalues therebetween, especially including 1,000; 2,000; 3,000; 4,000; 5,000; 6,000; 7,000; 8,000; 9,000; 10,000; 11,000; 12,000; 13,000; 14,000; 15,000; 16,000; 17,000; 18,000; 19,000; 20,000; 21,000; 22,000; 23,000; 24,000; 25,000; 26,000; 27,000; 28,000; 29,000; 30,000; 31,000; 32,000; 33,000 and 34,000 times that of sugar.

When the derivatives of the invention are used as a sweetener, an appropriate carrier and/or an appropriate bulking agent may be used as required. Preferably, the carrier is water, sugar, saccharin or starch. It is preferred to select the bulking agent from water, sugar alcohol, polydextrose, sugar and starch.

The derivatives of the invention can be used as a sweetener or an ingredient therefor, and further as a sweetener for products such as foods and the like to which a sweetness has to be imparted. Example of such products are confectionery, chewing gum, hygiene products, toiletries, cosmetics, pharmaceutical products and veterinary products for animals. The pharmaceutical product is preferably a tablet or a medicated liquid. Still further, they can be used in a method of imparting a sweetness to the products. This method can be, for example, a conventional method for using a sweetening ingredient for a sweetener in the sweeteners or the method of imparting a sweetness. Preferably, the method includes mixing a product with the above sweetener. Preferably, the product is selected from a confectionery, a chewing gum, a hygiene product, a cosmetic article, a pharmaceutical product and a veterinary product Preferably, a carrier and/or bulking agent as above are added.

Having generally described this invention, a further understanding can be obtained by reference to certain specific examples which are provided herein for purposes of illustration only, and are not intended to be limiting unless otherwise specified.

EXAMPLES

Example 1

Synthesis of N-[N-[3-(3-Hydroxy-4-methoxyphenyl)propyl ]-L-α-aspartyl]-L-phenylalanine 1-Methyl Ester Five milliliters of a solution of 4N-HCl/dioxane were added to 485 mg (1.0 mmol) of N-t-butoxycarbonyl-β-O-benzyl-α-L-aspartyl-L-phenylalanine methyl ester, and the mixture was stirred at room temperature for 1 hour. The reaction solution was concentrated under reduced pressure. Thirty milliliters of a 5% sodium hydrogencarbonate aqueous solution were added to the residue, and the mixture was extracted twice with 30 ml of ethyl acetate. The organic layer was washed with a saturated aqueous solution of sodium chloride, and dried over anhydrous magnesium sulfate. Then, magnesium sulfate was removed by filtration, and the filtrate was concentrated under reduced pressure to obtain 385 mg of β-O-benzyl-α-L-aspartyl-L-phenylalanine methyl ester as a viscous oil.

The β-O-benzyl-α-L-aspartyl-L-phenylalanine methyl ester (385 mg, 1.0 mmol) was dissolved in 15 ml of THF, and the solution was maintained at 0° C. To this were added 268 mg (1.0 mmol) of 3-benzyloxy-4-methoxycinnamaldehyde, 0.060 ml (1.0 mmol) of acetic acid and 318 mg (1.5 mmol) of NaB(OAc)$_3$H. The mixture was stirred at 0° C. for 1 hour and further overnight at room temperature. To the reaction solution were added 50 ml of a saturated aqueous solution of sodium hydrogen carbonate, and the mixture was extracted twice with 30 ml of ethyl acetate. The organic layer was washed with a saturated aqueous solution of sodium chloride, and dried over anhydrous magnesium sulfate. Then, magnesium sulfate was removed by filtration, and the filtrate was concentrated under reduced pressure. The residue was purified with PTLC (Preparative Thin Layer Chromatography) to obtain 523 mg (0.82 mmol) of N-[N-[3(3-benzyloxy-4-methoxyphenyl)propenyl]-β-O-benzyl-L-α-aspartyl]-L-phenylalanine 1-methyl ester as a viscous oil.

The N-[N-[3-(3-benzyloxy-4-methoxyphenyl)propenyl]-β-O-benzyl-L-α-aspartyl ]-L-phenylalanine 1-methyl ester (523 mg, 0.82 mmol) was dissolved in a mixed solvent of 30 ml of methanol and 1 ml of water, and 200 mg of 10% palladium carbon (water content 50%) were added thereto. The mixture was reduced under a hydrogen atmosphere at room temperature for 3 hours. The catalyst was removed by filtration, and the filtrate was concentrated under reduced pressure. In order to remove an odor adsorbed, the residue was purified with PTLC to obtain 228 mg (0.48 mmol) of N-(N-[3-(3-hydroxy-4 methoxyphenyl)propyl]-L-α-aspartyl]-L-phenylalanine 1-methyl ester as a solid.

$^1$HNMR (DMSO -$d_6$) δ: 1.50–1.60 (m, 2H), 2.15–2.40 (m, 6H), 2.87–2.97 (dd, 1H), 3.05–3.13 (dd, 1H), 3.37–3.43 (m, 1H), 3.62 (s, 3H), 3.71 (s, 3H), 4.50–4.60 (m, 1H), 6.25 (d, 1H), 6.60 (s, 1H), 6.79 (d, 1H), 7.18–7.30 (m, 5H), 8.52 (d, 1H), 8.80 (brs, 1H). ESI-MS 459.2 (MH$^+$).

Sweetening potency (relative to sugar): 20,000 times

Example 2

Synthesis of N-[N-[3-(3,4-Dimethoxyphenyl)propyl]-L-α-aspartyl]-L-phenylalanine 1-Methyl Ester Example 1 was repeated except that 3,4-dimethoxycinnamaldehyde was used instead of 3-benzyloxy-4-methoxycinnamaldehyde to obtain N-[N-[3-(3,4-dimethoxyphenyl)propyl]-L-α-aspartyl]-L-phenylalanine 1-methyl ester in a total yield of 48.7% as a solid.

$^1$HNMR (DMSO-$d_6$) δ: 1.52–1.62 (m, 2H), 2.18–2.50 (m, 6H), 2.86–2.76 (dd, 1H), 3.04–3.12 (dd, 1H), 3.37–3.44 (m, 1H), 3.62 (s, 3H), 3.71 (s, 3H), 3.73 (s, 3H), 4.52–4.62 (m, 1H), 6.66 (d, 1H), 6.76 (s, 1H), 6.83 (d, 1H), 7.18–7.30 (m, 5H), 8.50 (d, 1H). ESI-MS 473.2(MH$^+$).

Sweetening potency (relative to sugar): 2,500 times

Example 3

Synthesis of N-[N-[3-(3,4-Methylenedioxyphenyl)propyl ]-L-α-aspartyl]-L-phenylalanine 1-Methyl Ester Example 1 was repeated except that 3,4-methylenedioxycinnamaldehyde was used instead of 3-benzyloxy-4-methoxycinnamaldehyde to obtain N-[N-[3-(3,4-methylenedioxyphenyl)propyl]-L-α-aspartyl]-L-phenylalanine 1-methyl ester in a total yield of 42.1% as a solid.

$^1$HNMR (DMSO-$d_6$) δ: 1.48–1.60 (m, 2H), 2.14–2.48 (m, 6H), 2.86–2.96 (dd, 1H), 3.03–3.12 (dd, 1H), 3.37–3.43 (m, 1H), 3.62 (s, 3H), 4.54–4.59 (m, 1H), 5.94 (d, 1H), 5.95 (s, 1H), 6.61 (d, 1H), 6.74 (s, 1H), 6.78 (d, 1H), 7.15–7.30 (m, 5H), 8.47 (d, 1H). ESI-MS 457.2 (MH$^+$).

Sweetening potency (relative to sugar): 5,000 times

Example 4

Synthesis of N-[N-[3-(4-Hydroxyphenyl)propyl]-L-α-aspartyl]-L-phenylalanine 1-Methyl Ester Example 1 was repeated except that benzyloxycinnamaldehyde was used instead of 3-benzyloxy-4-methoxycinnamaldehyde to obtain N-[N-[3-(4-hydroxyphenyl)propyl]-L-α-aspartyl]-L-phenylalanine 1-methyl ester in a total yield of 40.6% as a solid.

$^1$HNMR (DMSO-$d_6$) δ: 1.48–1.60 (m, 2H), 2.14–2.43 (m, 6H), 2.86–2.96 (dd, 1H), 3.04–3.14 (dd, 1H), 3.37–3.42 (m, 1H), 3.62 (s, 3H), 4.52–4.62 (m, 1H), 6.65 (d, 1H), 6.93 (d, 2H), 7.16–7.29 (m, 5H), 8.49 (d, 1H), 9.12 (brs, 1H). ESI-MS 429.2 (MH$^+$).

Sweetening potency (relative to sugar): 5,000 times

Example 5

Synthesis of N-[N-[3-(4-Methoxyphenyl)propyl]-L-α-aspartyl]-L-phenylalanine 1-Methyl Ester (1)

Example 1 was repeated except that 4-methoxycinnamaldehyde was used instead of 3-benzyloxy-4-methoxycinnamaldehyde to obtain N-[N-[3-(4-methoxyphenyl)propyl]-L-α-aspartyl]-L-phenylalanine 1-methyl ester in a total yield of 50.0% as a solid.

$^1$HNMR (DMSO-$d_6$) δ: 1.50–1.62 (m, 2H), 2.16–2.48 (m, 6H), 2.84–2.94 (dd, 1H), 3.04–3.12 (dd, 1H), 3.38–3.44 (m, 1H), 3.62 (s, 3H), 3.71 (s, 3H), 4.52–4.62 (m, 1H), 6.83 (d, 1H), 7.08 (d, 2H), 7.17–7.29 (m, 5H), 8.50 (d, 1H). ESI-MS 443.3 (MH$^+$).

Sweetening potency (relative to sugar): 6,500 times

Example 6

Synthesis of N-[N-[3-(4-Methoxyphenyl)propyl]-L-α-aspartyl]-L-phenylalanine 1-Methyl Ester (2)

4-Methoxycinnamaldehyde (405 mg, 2.5 mmol), 735 mg (2.5 mmols) of aspartame and 350 mg of 10% palladium carbon (water content 50%) were added to a mixed solvent of 15 ml of methanol and 5 ml of water, and the mixture was stirred under a hydrogen atmosphere overnight at room temperature. The catalyst was removed by filtration, and the filtrate was concentrated under reduced pressure. To the residue were added 30 ml of ethyl acetate, and the mixture was stirred for a while. Then, the insoluble material was collected by filtration. The insoluble material collected was washed with a small amount of ethyl acetate. To this were added 50 ml of a mixed solvent of ethyl acetate and methanol (5:2), and the mixture was stirred for a while. The insoluble material was removed by filtration, and the filtrate was concentrated. Then, the overall residue was solidified. This was dried under reduced pressure, and then recrystallized from a mixed solvent of methanol and water to obtain N-[N-[3-(4-methoxyphenyl)propyl]-L-α-aspartyl]-L-phenylalanine 1-methyl ester in a total yield of 43.4% as a solid.

Example 7

Synthesis of N-[N-[3-(4-Ethoxyphenyl)propyl]-L-α-aspartyl]-L-phenylalanine 1-Methyl Ester Example 1 was repeated except that 4-ethoxycinnamaldehyde was used instead of 3-benzyloxy-4-methoxycinnamaldehyde to obtain N-[N-[3-(4ethoxyphenyl)propyl]-L-α-aspartyl]-L-phenylalanine 1-methyl ester in a total yield of 57.1% as a solid.

$^1$HNMR (DMSO-$d_6$) δ: 1.30 (t, 3H) 1.50–1.62 (m, 2H), 2.16–2.48 (m, 6H), 2.85–2.95 (dd, 1H), 3.02–3.12 (dd, 1H), 3.39–3.44 (m, 1H), 3.62 (s, 3H), 3.96 (q, 2H), 4.52–4.59 (m, 1H), 6.81 (d, 2H), 7.05 (d, 2H), 7.17–7.28 (m, 5H), 8.50 (d, 1H). ESI-MS 457.2 (MH$^+$).

Sweetening potency (relative to sugar): 1,500 times

Example 8

Synthesis of N-[N-[3-(3-Hydroxyphenyl)propyl]-L-α-aspartyl]-L-phenylalanine 1-Methyl Ester Example 1 was repeated except that 3-benzyloxycinnamaldehyde was used instead of 3-benzyloxy-4-methoxycinnamaldehyde to obtain N-[N-[3-(3-hydroxyphenyl)propyl]-L-α-aspartyl]-L-phenylalanine 1-methyl ester in a total yield of 46.6% as a solid.

$^1$HNMR (DMSO-$d_6$) δ: 1.50–1.62 (m, 1H), 2.10–2.48 (m, 6H), 2.87–2.96 (dd, 1H), 3.40–3.12 (dd, 1H), 3.33–3.38 (m, 1H), 3.62 (s, 3H), 4.52–4.60 (m, 1H), 6.53–6.60 (m, 3H) 7.04 (t, 1H), 7.17–7.30 (m, 5H), 8.50 (d, 1H), 9.40 (brs, 1H). ESI-MS 429.2 (MH$^+$).

Sweetening potency (relative to sugar): 8,000 times

Example 9

Synthesis of N-[N-[3-(3-Methoxyphenyl)propyl]-L-α-aspartyl]-L-phenylalanine 1-Methyl Ester Example 1 was repeated except that 3-methoxycinnamaldehyde was used instead of 3-benzyloxy-4-methoxycinnamaldehyde to obtain N-[N-[3-(3-methoxyphenyl)propyl]-L-α-aspartyl]-L-phenylalanine methyl ester in a total yield of 55.6% as a solid.

$^1$HNMR (DMSO-$d_6$) δ: 1.54–1.66 (m, 2H), 2.18–2.50 (m, 6H), 2.86–2.96 (dd, 1H), 3.02–3.12 (dd, 1H), 3.40–3.46 (m, 1H), 3.62 (s, 3H), 3.73 (s, 3H), 4.53–4.61 (m, 1H), 6.70–6.78 (m, 3H), 7.13–7.30 (m, 5H), 8.50 (d, 1H). ESI-MS 443.1 (MH$^+$).

Sweetening potency (relative to sugar): 3,500 times

Example 10

Synthesis of N-[N-[3-(3-Hydroxy-4-methoxyphenyl)propyl]-L-α-aspartyl]-L-tyrosine 1-Methyl Ester Example 1 was repeated except that N-t-butoxycarbonyl-β-O-benzyl-α-L-aspartyl-L-tyrosine methyl ester was used instead of N-t-butoxycarbonyl-β-O-benzyl-α-L-aspartyl-L-phenylalanine methyl ester to obtain N-[N-[3-(3-hydroxy-4-methoxyphenyl)propyl]-L-α-aspartyl]-L-tyrosine 1-methyl ester in a total yield of 45.4% as a solid.

$^1$HNMR (DMSO-$d_6$) δ: 1.52–1.64 (m, 2H), 2.24–2.48 (m, 6H), 2.74–2.84 (dd, 1H), 2.91–2.99 (dd, 1H), 3.47–3.54 (m, 1H), 3.61 (s, 3H), 3.72 (s, 3H), 4.45–4.53 (m, 1H), 6.54 (d, 1H), 6.60 (s, 1H), 6.65 (d, 2H), 6.79 (d, 1H), 6.98 (d, 2H), 8.54 (d, 1H), 8.78 (brs, 7H) 9.25 (brs, 1H). ESI-MS 475.2 (MH$^+$).

Sweetening potency (relative to sugar): 16,000 times

Example 11

Synthesis of N-(N-[3-(2-Hydroxy-4-methoxyphenyl)propyl]-L-α-aspartyl]-L-phenylalanine 1-Methyl Ester Example 1 was repeated except that 2-benzyloxy-4-methoxycinnamaldehyde was used instead of 3-benzyloxy-4-methoxycinnamaldehyde to obtain N-[N-[3-(2-hydroxy-4-methoxyphenyl)propyl]-L-α-aspartyl ]-L-phenylalanine 1-methyl ester in a total yield of 54.4% as a solid.

$^1$HNMR (DMSO-$d_6$) δ: 1.52–1.57 (m, 2H), 2.20–2.31 (m, 2H), 2.26–2.41 (m, 4H), 2.88–3.11 (m, 2H), 3.41–3.44 (m, 1H), 3.62 (s, 3H), 3.65 (s, 3H), 4.53–4.59 (m, 1H), 6.28–6.36 (m, 2H), 6.88–6.90 (d, 1H), 7.19–7.29 (m, 5H), 8.55 (d, 1H). ESI-MS 459.3 (MH$^+$).

Sweetening potency (relative to sugar): 20,000 times

Example 12

Synthesis of N-[N-[3-(2-Hydroxy-3-methoxyphenyl)propyl]-L-α-aspartyl]-L-phenylalanine 1-Methyl Ester Example 1 was repeated except that 2-benzyloxy-3-methoxycinnamaldehyde was used instead of 3-benzyloxy-4-methoxycinnamaldehyde to obtain N-[N-[3-(2-hydroxy-3-methoxyphenyl)propyl]-L-α-aspartyl]-L-phenylalanine 1-methyl ester in a total yield of 33.4% as a solid.

$^1$HNMR (DMSO-$d_6$) δ: 1.53–1.58 (m, 2H), 2.04–2.25 (m, 2H), 2.26–2.32 (m, 4H), 2.90–3.12 (m, 2H), 3.51–3.53 (m, 1H), 3.61 (s, 3H), 3.76 (s, 3H), 4.52–4.58 (m, 1H), 6.64–6.78 (m, 3H), 7.18–7.29 (m, 5H), 8.52 (d, 1H). ESI-MS 459.4 (MH$^+$).

Sweetening potency (relative to sugar): 10,000 times

Example 13

Synthesis of N-[N-[3-(2-Hydroxy-5-methoxyphenyl)propyl]-L-α-aspartyl]-L-phenylalanine 1-Methyl Ester Example 1 was repeated except that 2-benzyloxy-5-methoxycinnamaldehyde was used instead of 3-benzyloxy-4-methoxycinnamaldehyde to obtain N-[N-[3-(2-hydroxy-5-methoxyphenyl)propyl]-L-α-aspartyl]-L-phenylalanine 1-methyl ester in a total yield of 57.6% as a solid.

$^1$HNMR (DMSO-$d_6$) δ: 1.52–1.63 (m, 2H), 2.19–2.35 (m, 2H), 2.27–2.47 (m, 4H), 2.89–3.14 (m, 2H), 3.47–3.50 (m, 1H), 3.62 (s, 3H), 3.65 (s, 3H), 4.50–4.58 (m, 7H), 6.57–6.71 (m, 3H), 7.19–7.30 (m, 5H), 8.62 (d, 1H), 8.84 (brs, 1H). ESI-MS 459.3 (MH$^+$).

Sweetening potency (relative to sugar): 1,500 times

Example 14

Synthesis of N-[N-[3-(2-Hydroxy-4-methylphenyl)propyl]-L-α-aspartyl]-L-phenylalanine 1-Methyl Ester Example 1 was repeated except that 2-benzyloxy-4-methylcinnamaldehyde was used instead of 3-benzyloxy-4-methoxycinnamaldehyde to obtain N-[N-[3-(2-hydroxy-4-methylphenyl)propyl]-L-α-aspartyl]-L-phenylalanine 1-methyl ester in a total yield of 35.7% as a solid.

$^1$HNMR (DMSO-$d_6$) δ: 1.52–1.58 (m, 2H), 2.17 (s, 3H), 2.19–2.32 (m, 2H), 2.37–2.44 (m, 4H), 2.87–3.11 (m, 2H), 3.39–3.42 (m, 1H), 3.62 (s, 3H), 4.53–4.58 (m, 1H), 6.50 (d, 2H), 6.58 (s, 1H), 6.80 (d, 1H), 7.15–7.29 (m, 5H), 8.54 (d, 1H). ESI-MS 443.3 (MH$^+$).

Sweetening potency (relative to sugar): 30,000 times

Example 15

Synthesis of N-[N-[3-(2,4-Dimethoxyphenyl)propyl]-L-α-aspartyl]-L-phenylalanine 1-Methyl Ester Example 1 was repeated except that 2,4-dimethoxycinnamaldehyde was used instead of 3-benzyloxy-4-methoxycinnamaldehyde to obtain N-[N-[3-

(2,4-dimethoxyphenyl)propyl]-L-α-aspartyl]-L-phenylalanine 1-methyl ester in a total yield of 32.4% as a solid.

¹HNMR (DMSO-d₆) δ: 1.50–1.54 (m, 2H), 2.20–2.31 (m, 2H), 2.25–2.43 (m, 4H), 2.88–3.12 (m, 2H), 3.44–3.82 (m, 1H), 3.62 (s, 3H), 3.72 (s, 3H), 3.75 (s, 4.54–4.59 (m, 1H), 6.40–6.50 (m, 2H), 6.96–6.98 (m, 1H), 7.19–7.29 (m, 5H), 8.50 (d, 1H). ESI-MS 473.3 (MH⁺).

Sweetening potency (relative to sugar): 4,000 times

Example 16

Synthesis of N-[N-[3-(2-Ethoxy-4-methoxyphenyl)propyl]-L-α-aspartyl]-L-phenylalanine 1-Methyl Ester Example 1 was repeated except that 2-ethoxy-4-methoxycinnamaldehyde was used instead of 3-benzyloxy-4-methoxycinnamaldehyde to obtain N-[N-[3-(2-ethoxy-4-methoxyphenyl)propyl]-L-α-aspartyl ]-L-phenylalanine 1-methyl ester in a total yield of 35.6% as a solid.

¹HNMR (DMSO-d₆) δ: 1.30–1.34 (t, 3H), 1.50–1.57 (m, 2H), 2.10–2.41 (m, 2H), 2.24–2.43 (m, 4H), 2.87–3.11 (m, 2H), 3.38–3.42 (m, 1H), 3.62 (s, 3H), 3.70–4.03 (q, 2H), 4.53–4.60 (m, 1H), 6.40–6.48 (m, 2H), 6.96–6.98 (m, 1H), 7.19–7.29 (m, 5H), 8.51 (d, 1H). ESI-MS 487.4 (MH⁺).

Sweetening potency (relative to sugar): 2,500 times

Example 17

Synthesis of N-(N-[3-(3-Methyl-4-hydroxyphenyl)propyl]-L-α-aspartyl]-L-phenylalanine 1-Methyl Ester Example 1 was repeated except that 3-methyl-4-benzyloxycinnamaldehyde was used instead of 3-benzyloxy-4-methoxycinnamaldehyde to obtain N-[N-[3-(3-methyl-4-hydroxyphenyl)propyl]-L-α-aspartyl]-L-phenylalanine 1-methyl ester in a total yield of 32.2% as a solid.

¹HNMR (DMSO-d₆) δ: 1.50–1.58 (m, 2H), 2.08 (s, 3H), 2.09–2.30 (m, 2H), 2.26–2.38 (m, 4H), 2.89–3.09 (m, 2H), 3.35–3.42 (m, 1H), 3.62 (s, 3H), 4.54–4.59 (m, 1H), 6.3–6.83 (m, 3H), 7.19–7.28 (m, 5H), 8.52 (d, 1H), 9.04 (brs, 1H). ESI-MS 443.4 (MH⁺).

Sweetening potency (relative to sugar): 35,000 times

Example 18

Synthesis of N-[N-[3-(3-Hydroxy-4-methylphenyl)propyl]-L-α-aspartyl]-L-phenylalanine 1-Methyl Ester Example 1 was repeated except that 3-benzyloxy-4-methylcinnamaldehyde was used instead of 3-benzyloxy-4-methoxycinnamaldehyde to obtain N-[N-[3-(3-hydroxy-4-methylphenyl)propyl]-L-α-aspartyl]-L-phenylalanine 1-methyl ester in a total yield of 46.9% as a solid.

¹HNMR (DMSO-d₆) δ: 1.51–1.58 (m, 2H), 2.06 (s, 3H), 2.18–2.32 (m, 2H), 2.24–2.393 (m, 4H), 2.87–3.11 (m, 2H), 3.39–3.43 (m, 1H), 3.62 (s, 3H), 4.54–4.60 (m, 1H), 6.47–6.58 (m, 2H), 6.90–6.93 (m, 1H), 7.12–7.29 (m, 5H), 8.52 (d, 1H), 9.12 (brs, 1H). ESI-MS 443.4 (MH⁺).

Sweetening potency (relative to sugar): 15,000 times

Example 19

Synthesis of N-[N-(3-(3-Methyl-4-methoxyphenyl)propyl]-L-α-aspartyl]-L-phenylalanine 1-Methyl Ester Example 1 was repeated except that 3-methyl-4-methoxycinnamaldehyde was used instead of 3-benzyloxy-4-methoxycinnamaldehyde to obtain N-[N-[3-(3-methyl-4-methoxyphenyl)propyl]-L-α-aspartyl]-L-phenylalanine 1-methyl ester in a total yield of 34.0% as a solid.

¹HNMR (DMSO-d₆) δ: 1.52–1.59 (m, 2H), 2.11 (s, 3H), 2.20–2.38 (m, 2H), 2.26–2.433 (m, 4H), 2.89–3.10 (m, 2H), 3.39–3.43 (m, 1H), 3.62 (s, 3H), 3.73 (s, 3H), 4.52–4.59 (m, 1H), 6.79–6.82 (m, 1H), 6.92–6.94 (m, 2H), 7.1907.28 (m, 5H), 8.53 (d, 1H). ESI-MS 457.4 (MH⁺).

Sweetening potency (relative to sugar): 8,000 times

Example 20

Synthesis of N-[N-[3-(3,5-Dimethoxyphenyl)propyl]-L-α-aspartyl]-L-phenylalanine 1-Methyl Ester Example 1 was repeated except that 3,5-dimethoxycinnamaldehyde was used instead of 3-benzyloxy-4-methoxycinnamaldehyde to obtain N-[N-[3-(3,5-dimethoxyphenyl)propyl]-L-α-aspartyl]-L-phenylalanine 1-methyl ester in a total yield of 41.0% as a solid.

¹HNMR (DMSO-d₆) δ: 1.56–1.62 (m, 2H), 2.18–2.38 (m, 2H), 2.25–2.497 (m, 4H), 2.88–3.11 (m, 2H), 3.38–3.44 (m, 1H), 3.62 (s, 3H), 3.71 (s, 6H), 4.53–4.59 (m, 1H), 6.30–6.35 (m, 3H), 7.19–7.28 (m, 5H), 8.55 (d, 1H). ESI-MS 473.3 (MH⁺).

Sweetening potency (relative to sugar): 800 times

Example 21

Synthesis of N-[N-[3-(4-(2-Hydroxyethoxy)phenyl)propyl]-L-α-aspartyl]-L-phenylalanine 1-Methyl Ester Example 1 was repeated except that 4-(2-hydroxyethxy)cinnamaldehyde was used instead of 3-benzyloxy-4-methoxycinnamaldehyde to obtain N-(N-[3-(4-(2-hydroxyethoxy)phenyl)propyl]-L-α-aspartyl]-L-phenylalanine 1-methyl ester in a total yield of 33.8% as a solid.

¹HNMR (DMSO-d₆) δ: 1.52–1.60 (m, 2H), 2.18–2.35 (m, 2H), 2.24–2.47 (m, 4H), 3.38–3.43 (m, 1H), 3.62 (s, 3H), 3.67–3.71 (m, 2H), 3.92–3.95 (m, 2H), 4.53–4.59 (m, 1H), 6.82–6.85 (d, 2H), 7.05–7.07 (d, 2H), 7.19–7.29 (m, 5H), 8.51 (d, 1H). ESI-MS 473.3 (MH⁺).

Sweetening potency (relative to sugar): 1,000 times

Example 22

Synthesis of N-[N-[3-(4-Methylphenyl)propyl ]-L-α-aspartyl]-L-phenylalanine 1-Methyl Ester Example 1 was repeated except that 4-methylcinnamaldehyde was used instead of 3-benzyloxy-4-methoxycinnamaldehyde to obtain N-(N-[3-(4-methylphenyl)propyl]-L-α-aspartyl]-L-phenylalanine 1-methyl ester in a total yield of 54.1% as a solid.

¹HNMR (DMSO-d₆) δ: 1.50–1.63 (m, 2H), 2.18–2.39 (m, 2H), 2.25 (m, 2H), 2.25 (s, 3H), 2.29–2.46 (m, 4H), 2.87–3.11 (m, 2H), 3.41–3.47 (m, 1H), 3.61 (s, 3H), 4.53–4.61 (m, 1H), 7.03–7.09 (m, 4H), 7.17–7.29 (m, 5H), 8.58 (d, 1H). ESI-MS 427.4 (MH⁺).

Sweetening potency (relative to sugar): 4,000 times

Effects of Invention

The novel aspartyl dipeptide ester derivatives of the invention have especially an excellent sweetening potency in comparison with conventional sweeteners. The invention can provide novel chemical substances having excellent taste properties as a sweetener. Accordingly, such novel derivatives in the present invention can be used as a sweetener, and also can impart a sweetness to products such as beverages and foods requiring a sweetness.

The priority documents of the present application, Japanese patent application No. 10-97701, filed Apr. 9, 1998; Japanese patent application No. 11-38190, filed Feb. 17, 1999 and PCT application No. PCT/JP99/01210, filed Mar. 11, 1999, are incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A compound of Formula (1):

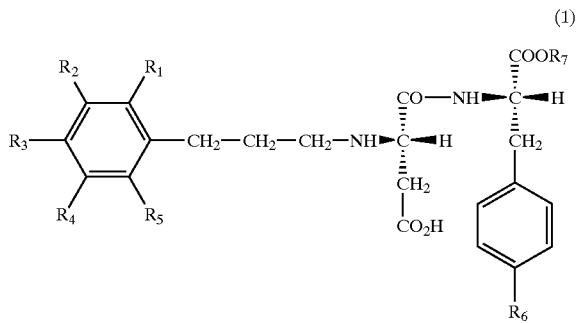

(1)

wherein $R_1$, $R_2$, $R_3$, $R_4$ and $R_5$ independently represent a substituent selected from the group consisting of a hydrogen atom, a hydroxyl group, an alkoxy group having from 1 to 3 carbon atoms, an alkyl group having from 1 to 3 carbon atoms and a hydroxyalkyloxy group having 2 or 3 carbon atoms; or $R_1$ and $R_2$, or $R_2$ and $R_3$ together form a methylenedioxy group, wherein $R_4$, $R_5$, and $R_1$ or $R_3$ which do not form said methylenedioxy group independently represent a substituent selected from the group consisting of a hydrogen atom, a hydroxyl group, an alkoxy group having from 1 to 3 carbon atoms, an alkyl group having from 1 to 3 carbon atoms and a hydroxyalkyloxy group having 2 or 3 carbon atoms;

$R_6$ represents a hydrogen atom or a hydroxyl group; and $R_7$ represents a substituent selected from the group consisting of a methyl group, an ethyl group, an isopropyl group, an n-propyl group and a t-butyl group;

wherein $R_1$ to $R_5$ do not all represent hydrogen atoms; and wherein $R_2$ or $R_4$ do not represent a methoxy group if $R_3$ represents a hydroxyl group; and the salt thereof; and wherein said compound of Formula (1) has a sweetening potency greater than 5,000 times the sweetening potency of sugar.

2. The compound according to claim 1, wherein $R_2$ is a hydroxyl group, $R_3$ is a methoxy group, $R_1$, $R_4$, $R_5$ and $R_6$ are hydrogen atoms, and $R_7$ is a methyl group.

3. The compound according to claim 1, wherein $R_2$ and $R_3$ are methoxy groups, $R_1$, $R_4$, $R_5$ and $R_6$ are hydrogen atoms, and $R_7$ is a methyl group.

4. The compound according to claim 1, wherein $R_2$ and $R_3$ together form a methylenedioxy group, $R_1$, $R_4$, $R_5$ and $R_6$ are hydrogen atoms, and $R_7$ is a methyl group.

5. The compound according to claim 1, wherein $R_3$ is a hydroxyl group, $R_1$, $R_2$, $R_4$, $R_5$ and $R_6$ are hydrogen atoms, and $R_7$ is a methyl group.

6. The compound according to claim 1, wherein $R_3$ is a methoxy group, $R_1$, $R_2$, $R_4$, $R_5$ and $R_6$ are hydrogen atoms, and $R_7$ is a methyl group.

7. The compound according to claim 1, wherein $R_3$ is an ethoxy group, $R_1$, $R_2$, $R_4$, $R_5$ and $R_6$ are hydrogen atoms, and $R_7$ is a methyl group.

8. The compound according to claim 1, wherein $R_2$ is a hydroxyl group, $R_1$, $R_3$, $R_4$, $R_5$ and $R_6$ are hydrogen atoms, and $R_7$ is a methyl group.

9. The compound according to claim 1, wherein $R_2$ is a methoxy group, $R_1$, $R_3$, $R_4$, $R_5$ and $R_6$ are hydrogen atoms, and $R_7$ is a methyl group.

10. The compound according to claim 1, wherein $R_3$ is a methoxy group, $R_2$ and $R_6$ are hydroxyl groups, $R_1$, $R_4$ and $R_5$ are hydrogen atoms, and $R_7$ is a methyl group.

11. The compound according to claim 1, wherein $R_1$ is a hydroxyl group, $R_3$ is a methoxy group, $R_2$, $R_4$, $R_5$ and $R_6$ are hydrogen atoms, and $R_7$ is a methyl group.

12. The compound according to claim 1, wherein $R_1$ is a hydroxyl group, $R_2$ is a methoxy group, $R_3$, $R_4$, $R_5$ and $R_6$ are hydrogen atoms, and $R_7$ is a methyl group.

13. The compound according to claim 1, wherein $R_1$ is a hydroxyl group, $R_4$ is a methoxy group, $R_2$, $R_3$, $R_5$ and $R_6$ are hydrogen atoms, and $R_7$ is a methyl group.

14. The compound according to claim 1, wherein $R_1$ is a hydroxyl group, $R_3$ and $R_7$ are methyl groups, and $R_2$, $R_4$, $R_5$ and $R_6$ are hydrogen atoms.

15. The compound according to claim 1, wherein $R_1$ and $R_3$ are methoxy groups, $R_2$, $R_4$, $R_5$ and $R_6$ are hydrogen atoms, and $R_7$ is a methyl group.

16. The compound according to claim 1, wherein $R_1$ is an ethoxy group, $R_3$ is a methoxy group, $R_2$, $R_4$, $R_5$ and $R_6$ are hydrogen atoms, and $R_7$ is a methyl group.

17. The compound according to claim 1, wherein $R_2$ and $R_7$ are methyl groups, $R_3$ is a hydroxyl group, and $R_1$, $R_4$, $R_5$ and $R_6$ are hydrogen atoms.

18. The compound according to claim 1, wherein $R_2$ is a hydroxyl group, $R_3$ and $R_7$ are methyl groups, and $R_1$, $R_4$, $R_5$ and $R_6$ are hydrogen atoms.

19. The compound according to claim 1, wherein $R_2$ and $R_7$ are methyl groups, $R_3$ is a methoxy group, and $R_1$, $R_4$, $R_5$ and $R_6$ are hydrogen atoms.

20. The compound according to claim 1, wherein $R_2$ and $R_4$ are methoxy groups, $R_1$, $R_3$, $R_5$ and $R_6$ are hydrogen atoms, and $R_7$ is a methyl group.

21. The compound according to claim 1, wherein $R_3$ is a 2-hydroxyethoxy group, $R_1$, $R_2$, $R_4$, $R_5$ and $R_6$ are hydrogen atoms, and $R_7$ is a methyl group.

22. The compound according to claim 1, wherein $R_3$ and $R_7$ are methyl groups, and $R_1$, $R_2$, $R_4$, $R_5$ and $R_6$ are hydrogen atoms.

23. The compound according to claim 1, wherein said salt is selected from the group consisting of an alkali metal salt, an alkaline earth metal salt, an ammonium salt, an amino acid salt, an inorganic salt, an organic salt, a saccharin salt, an acesulfame salt, a cyclamic acid salt and a glycyrrhizic acid salt.

24. The compound according to claim 23, wherein said alkali metal salt is a sodium salt, a potassium salt or a mixture thereof.

25. The compound according to claim 23, wherein said alkaline earth metal salt is a calcium salt, a magnesium salt or a mixture thereof.

26. The compound according to claim 23, wherein said amino acid salt is a salt of lysine, a salt of arginine or a mixture thereof.

27. The compound according to claim 23, wherein said inorganic salt is a chloride or a sulfate.

28. The compound according to claim 23, wherein said organic salt is a salt of citric acid, a salt of acetic acid or a mixture thereof.

29. A sweetener, comprising the compound of claim 1 and/or the salt thereof.

30. The sweetener of claim 29, wherein said salt is selected from the group consisting of an alkali metal salt, an alkaline earth metal salt, an ammonium salt, and amino acid salt, an inorganic salt and an organic salt.

31. The sweetener according to claim 29, wherein said sweetener has a sweetening potency of from 800 times to 35000 times the sweetening potency of sugar.

32. The sweetener according to claim 29, wherein said sweetener has a sweetening potency of from 15000 times to 35000 times the sweetening potency of sugar.

33. The sweetener according to claim 29, further comprising a carrier and/or a bulking agent.

34. The sweetener according to claim 33, wherein said carrier is selected from the group consisting of water, sugar, saccharin, starch and mixtures thereof.

35. The sweetener according to claim 33, wherein said bulking agent is selected from the group consisting of water, sugar alcohol, polydextrose, sugar, starch and mixtures thereof.

36. A product having a sweetness, comprising:
  a confectionery; and
  the sweetener according to claim 29.

37. A product having a sweetness, comprising:
  a chewing gum; and
  the sweetener according to claim 29.

38. A product having a sweetness, comprising:
  a hygiene product; and
  the sweetener according to claim 29.

39. A product having a sweetness, comprising:
  a cosmetic article; and
  the sweetener according to claim 29.

40. A product having a sweetness, comprising:
  a pharmaceutical product; and
  the sweetener according to claim 29.

41. The product according to claim 40, wherein said pharmaceutical product is selected from the group consisting of a tablet and a medicated liquid.

42. A product having a sweetness, comprising:
  a veterinary product; and
  the sweetener according to claim 29.

43. A method of imparting sweetness, comprising:
  mixing a product with the sweetener according to claim 29.

44. The method according to claim 43, wherein said product is selected from the group consisting of a confectionery, a chewing gum, a hygiene product, a cosmetic article, a pharmaceutical product and a veterinary product.

45. The method according to claim 43, further comprising:
  adding a carrier and/or a bulking agent.

46. The method according to claim 45, wherein said carrier is selected from the group consisting of water, sugar, saccharin, starch and mixtures thereof.

47. The method according to claim 45, wherein said bulking agent is selected from the group consisting of water, sugar alcohol, polydextrose, sugar, starch and mixtures thereof.

48. The compound of claim 1, which is selected from the group consisting of N-[N-[3-(3-hydroxy-4-methoxyphenyl)propyl]-L-α-aspartyl]-L-phenylalanine 1-methyl ester; N-[N-[3-(3,4-methylenedioxyphenyl)propyl]-L-α-aspartyl]-L-phenylalanine 1-methyl ester; N-[N-[3-(4-hydroxyphenyl)propyl]-L-α-aspartyl]-L-phenylalanine 1-methyl ester; N-[N-[3-(4-methoxyphenyl)propyl]-L-α-aspartyl]-L-phenylalanine 1-methyl ester; N-[N-[3-(3-hydroxyphenyl)propyl]-L-α-aspartyl]-L-phenylalanine 1-methyl ester; N-[N-[3-(3-methoxyphenyl)propyl]-L-α-aspartyl]-L-phenylalanine 1-methyl ester; N-[N-[3-(3-hydroxy-4-methoxyphenyl)propyl]-L-α-aspartyl]-L-tyrosine 1-methyl ester; N-(N-[3-(2-hydroxy-4-methoxyphenyl)propyl]-L-α-aspartyl]-L-phenylalanine 1-methyl ester; N-[N-[3-(2-hydroxy-3-methoxyphenyl)propyl]-L-α-aspartyl]-L-phenylalanine 1-methyl ester; N-[N-[3-(2-hydroxy-4-methylphenyl)propyl]-L-α-aspartyl]-L-phenylalanine 1-methyl ester; N-[N-[3-(2,4-dimethoxyphenyl)propyl]-L-α-aspartyl]-L-phenylalanine 1-methyl ester; N-(N-[3-(3-methyl-4-hydroxyphenyl)propyl]-L-α-aspartyl]-L-phenylalanine 1-methyl ester; N-[N-[3-(3-hydroxy-4-methylphenyl)propyl]-L-α-aspartyl]-L-phenylalanine 1-methyl ester; N-[N-(3-(3-methyl-4-methoxyphenyl)propyl]-L-α-aspartyl]-L-phenylalanine 1-methyl ester; N-[N-[3-(4-methylphenyl)propyl]-L-α-aspartyl]-L-phenylalanine 1-methyl ester; and salts thereof.

49. The sweetener of claim 29, wherein said compound is is selected from the group consisting of N-[N-[3-(3-hydroxy-4-methoxyphenyl)propyl]-L-α-aspartyl]-L-phenylalanine 1-methyl ester; N-[N-[3-(3,4-methylenedioxyphenyl)propyl]-L-α-aspartyl]-L-phenylalanine 1-methyl ester; N-[N-[3-(4-hydroxyphenyl)propyl]-L-α-aspartyl]-L-phenylalanine 1-methyl ester; N-[N-[3-(4-methoxyphenyl)propyl]-L-α-aspartyl]-L-phenylalanine 1-methyl ester; N-[N-[3-(3-hydroxyphenyl)propyl]-L-α-aspartyl]-L-phenylalanine 1-methyl ester; N-[N-[3-(3-methoxyphenyl)propyl]-L-α-aspartyl]-L-phenylalanine 1-methyl ester; N-[N-[3-(3-hydroxy-4-methoxyphenyl)propyl]-L-α-aspartyl]-L-tyrosine 1-methyl ester; N-(N-[3-(2-hydroxy-4-methoxyphenyl)propyl]-L-α-aspartyl]-L-phenylalanine 1-methyl ester; N-[N-[3-(2-hydroxy-3-methoxyphenyl)propyl]-L-α-aspartyl]-L-phenylalanine 1-methyl ester; N-[N-[3-(2-hydroxy-4-methylphenyl)propyl]-L-α-aspartyl]-L-phenylalanine 1-methyl ester; N-[N-[3-(2,4-dimethoxyphenyl)propyl]-L-α-aspartyl]-L-phenylalanine 1-methyl ester; N-(N-[3-(3-methyl-4-hydroxyphenyl)propyl]-L-α-aspartyl]-L-phenylalanine 1-methyl ester; N-[N-[3-(3-hydroxy-4-methylphenyl)propyl]-L-α-aspartyl]-L-phenylalanine 1-methyl ester; N-[N-(3-(3-methyl-4-methoxyphenyl)propyl]-L-α-aspartyl]-L-phenylalanine 1-methyl ester; N-[N-[3-(4-methylphenyl)propyl]-L-α-aspartyl]-L-phenylalanine 1-methyl ester; and salts thereof.

50. The compound of claim 1, which has a sweetening potency greater than 8,000 times the sweetening potency of sugar.

51. The compound of claim 1, which has a sweetening potency greater than 10,000 times the sweetening potency of sugar.

52. The sweetener of claim 29, wherein the compound of Formula (1) has a sweetening potency greater than 8,000 times the sweetening potency of sugar.

53. The sweetener of claim 29, wherein the compound of Formula (1) has a sweetening potency greater than 10,000 times the sweetening potency of sugar.

* * * * *